(12) United States Patent
Stürzl et al.

(10) Patent No.: US 6,894,157 B2
(45) Date of Patent: May 17, 2005

(54) GUANYLATE BINDING PROTEIN (GBP-1) AS INHIBITOR OF CELL PROLIFERATION AND MOLECULAR MARKER FOR THE DETERMINATION OF THE STAGE OF CELLULAR DIFFERENTIATION

(75) Inventors: Michael Stürzl, München (DE); Emmanuelle Cornali, München (DE)

(73) Assignee: Michael Sturzl, Erlangen (DE)

( * ) Notice: Subject to any disclaimer, the term of this patent is extended or adjusted under 35 U.S.C. 154(b) by 173 days.

(21) Appl. No.: 09/791,502

(22) Filed: Feb. 23, 2001

(65) Prior Publication Data

US 2002/0115138 A1 Aug. 22, 2002

Related U.S. Application Data

(63) Continuation-in-part of application No. PCT/EP99/06148, filed on Aug. 23, 1999.

(30) Foreign Application Priority Data

Aug. 26, 1998 (DK) .......................................... 1998 01081
Oct. 1, 1998 (DK) .......................................... 1998 01241

(51) Int. Cl.[7] .......................... C07H 21/04; C12P 21/06; C12N 15/74; C12N 5/02; C07K 14/00
(52) U.S. Cl. .................. 536/24.3; 435/69.1; 435/320.1; 435/325; 530/350
(58) Field of Search ........................ 530/350; 435/69.1, 435/320.1, 325; 536/243

(56) References Cited

U.S. PATENT DOCUMENTS

| | | | | |
|---|---|---|---|---|
| 5,256,553 A | * | 10/1993 | Overell | ........................ 435/456 |
| 5,328,470 A | * | 7/1994 | Nabel et al. | ............ 604/101.03 |
| 5,652,122 A | | 7/1997 | Frankel et al. | |
| 5,670,617 A | | 9/1997 | Frankel et al. | |
| 5,674,980 A | | 10/1997 | Frankel et al. | |
| 5,747,641 A | | 5/1998 | Frankel et al. | |
| 5,804,604 A | | 9/1998 | Frankel et al. | |
| 5,871,965 A | | 2/1999 | Bandman et al. | |
| 6,265,189 B1 | * | 7/2001 | Paoletti et al. | .............. 435/70.1 |

FOREIGN PATENT DOCUMENTS

| WO | WO 98/18911 | 5/1998 |
|---|---|---|
| WO | WO 00/12737 | 3/2000 |

OTHER PUBLICATIONS

GenBank accesion No. AA296543, Kerlavage et al., 1997.*
Anderson, Sylvia L. et al., 1999, "Interferon–Induced Guanylate Binding Protein–1 (GBP–1) Mediates an Antiviral Effect against Vesicular Stomatitis Virus and Encephalomyocarditis Virus", *Virology*, vol. 256, pp. 8–14.
Cheng, Yih–Shyum E. et al., 1983, "Interferon Induction of Fibroblast Proteins with Guanylate Binding Activity", *The Journal of Biological Chemistry*, vol. 258, pp. 7746–7750.
Cheng, Yih–Shyum E. et al., 1991, "Interferon–Induced Guanylate–Binding Proteins Lack an N (T) KXD Consensus Motif and Bind GMP in Addition to GDP and GTP", *Molecular and Cellular Biology*, vol. 11, No. 9, pp. 4717–4725.
Cheng, Yih–Shyun E. et al., 1988, "Accumulation of Guanylate Binding Proteins in Patients Treated with Interferons", *Journal of Interferon Research*, vol. 8, pp. 385–391.
Decker, Thomas et al., 1991, "Two Distinct Alpha–Interferon–Dependent Signal Transduction Pathways May Contribute to Activation of Transcription of the Guanylate–Binding Protein Gene", *Molecular and Cellular Biology*, vol. 11, No. 10, pp. 5147–5153.
Lew, Daniel J. et al., 1991, "Overlapping Elements in the Guanylate– Binding Protein Gene Promoter Mediate Transcriptional Induction by Alpha and Gamma Interferons", *Molecular and Cellular Biology*, vol. 11, No. 01, pp. 182–191.
Schwemmle, Martin et al., 1994, "The Interferon–induced 67–kDa Guanylate–binding Protein (hGBP1) Is a GTPase That Converts GTP to GMP", *The Journal of Biological Chemistry*, vol. 269, No. 15, pp. 11299–11305.

* cited by examiner

*Primary Examiner*—Janet Andres
(74) *Attorney, Agent, or Firm*—Hamilton, Brook, Smith & Reynolds, P.C.

(57) ABSTRACT

The present invention relates to an expression vector comprising the Guanylate Binding Protein 1 (GBP-1) gene or parts thereof. The introduction of said vector comprising said gene or parts thereof in sense or antisense orientation into cells can be used to induce phenotypical changes of said cells and can, thus, be used for modulation of cell differentiation. Additionally, the present invention provides, inter alia, a method for determination of the stage of cellular differention by using GBP-1 gene expression as a marker.

13 Claims, 2 Drawing Sheets

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Primer for the amplification of a sequence of
      the human GBP-1 gene

<400> SEQUENCE: 1 cttttctcc ttagttcacg                                                    20

<210> SEQ ID NO 2
<211> LENGTH: 20
<212> TYPE: DNA
<213> ORGANISM: Artificial Sequence
<220> FEATURE:
<223> OTHER INFORMATION: Primer for the amplification of a sequence of
      the human GBP-1 gene

<400> SEQUENCE: 2
tcccttgtct gttcttttc                                                    20

<210> SEQ ID NO 3
<211> LENGTH: 33
<212> TYPE: DNA
<213> ORGANISM: Artificial Sequence
<220> FEATURE:
<223> OTHER INFORMATION: Primer for the amplification of a sequence of
      the human GBP-1 gene

<400> SEQUENCE: 3

```
tcccttgtct gttcttttc tccttagttc acg                          33
```

<210> SEQ ID NO 4
<211> LENGTH: 32
<212> TYPE: DNA
<213> ORGANISM: Artificial Sequence
<220> FEATURE:
<223> OTHER INFORMATION: Primer for the amplification of a sequence of
      the human GBP-1 gene

<400> SEQUENCE: 4

```
gctctagatt agcttatggt acatgccttt cg                          32
```

<210> SEQ ID NO 5
<211> LENGTH: 35
<212> TYPE: DNA
<213> ORGANISM: Artificial Sequence
<220> FEATURE:
<223> OTHER INFORMATION: Primer for the amplification of a sequence of
      the human GBP-1 gene

<400> SEQUENCE: 5

```
cggaattcgc cgccatggca tcagagatcc acatg                       35
```

<210> SEQ ID NO 6
<211> LENGTH: 10
<212> TYPE: DNA
<213> ORGANISM: Artificial Sequence
<220> FEATURE:
<223> OTHER INFORMATION: Primer for the amplification of a sequence of
      the human GBP-1 gene

<400> SEQUENCE: 6

```
tcgatacagg                                                   10
```

GUANYLATE BINDING PROTEIN (GBP-1) AS INHIBITOR OF CELL PROLIFERATION AND MOLECULAR MARKER FOR THE DETERMINATION OF THE STAGE OF CELLULAR DIFFERENTIATION

RELATED APPLICATION(S)

This application is a continuation-in-part of International Application No. PCT/EP99/06148, which designated the United States and was filed on Aug. 23, 1999, published in English, which claims the benefit of Danish Application No. PA 1998 01241, filed on Oct. 1, 1998 and Danish Application No. PA 1998 01081, filed Aug. 26, 1998.

The entire teachings of the above application(s) are incorporated herein by reference.

BACKGROUND OF THE INVENTION

Figure 1:
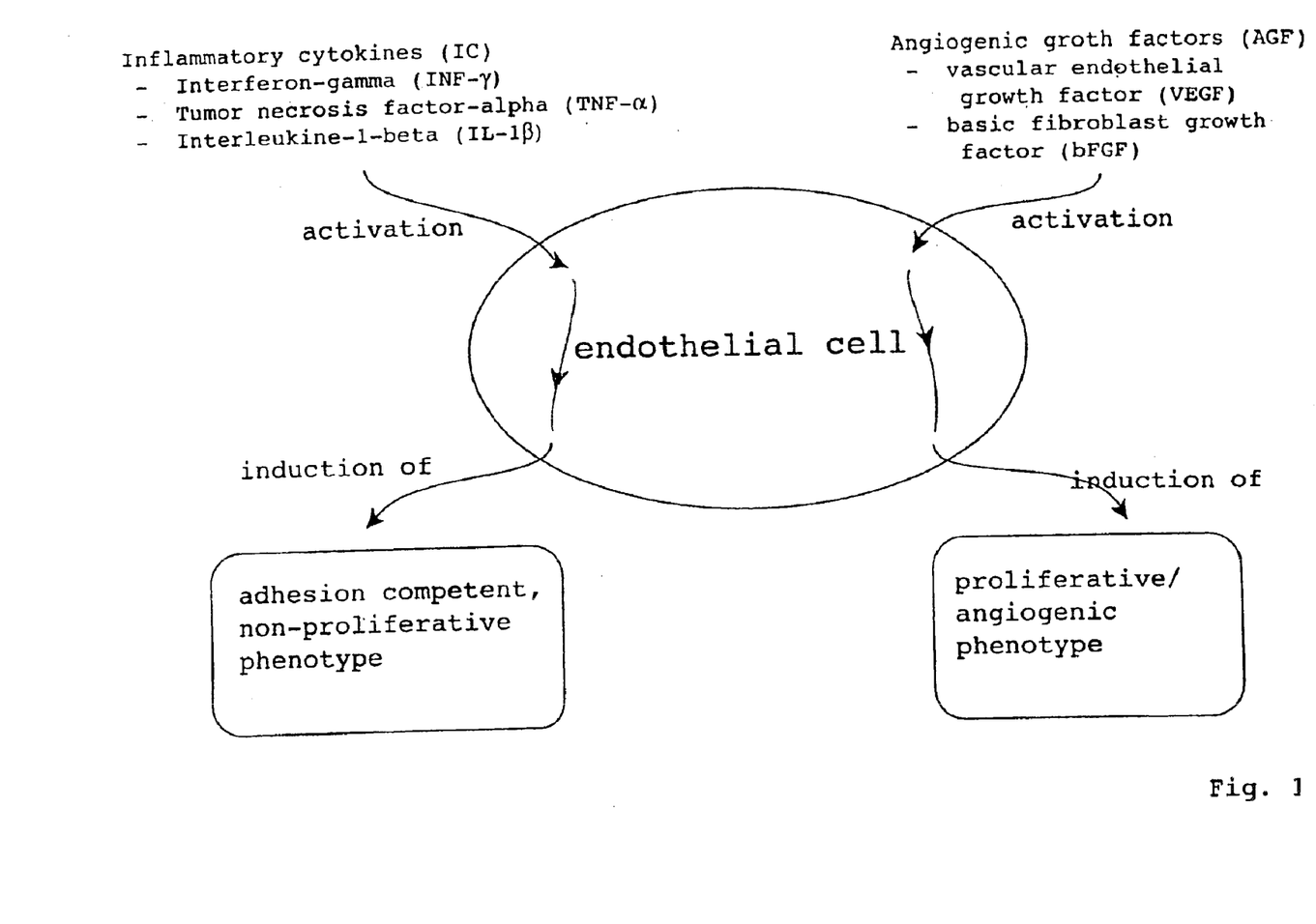
FIG. 1 is a schematic showing two different activated phenotypes of endothelial cells.

A healthy luminal endothelium consists of quiescent endothelial cells that provide a regularly organized and relatively non-adhesive surface towards the blood constituents. However, this interface is dynamic, and the endothelial cell phenotype can undergo profound changes leading to an activated phenotype. The activated phenotype represents a time- and dose-integrated response to various stimuli originating from the circulating blood and/or from neighboring cells and tissues. Among these stimuli, inflammatory cytokines (IC) such as interleukin-1 beta (IL-1β), tumor necrosis factor-alpha (TNF-α) and interferon-gamma (IFN-γ), or angiogenic growth factors (AGF) such as vascular endothelial growth factor (VEGF) or basic fibroblast growth factor (bFGF) have been shown to activate endothelial cells by altering their pattern of gene expression and thereby, altering their properties and phenotype. With respect to the biological activities of endothelial cells two different activated phenotypes can be distinguished (FIG. 1). On the one hand, there is the adhesion-competent and non-proliferative phenotype, which can be induced by the IC. The other quite opposite phenotype is characterized by increased motility and cell proliferation, which is induced by AGF. In an in vivo situation all cytokines and growth factors potentially activate the endothelial cells. Consequently, the phenotype of endothelial cells will depend on their ability to respond to the local balance of inflammatory cytokines and growth factor concentrations.

The IC such as IL-1β, TNF-α or IFN-γ are mainly secreted by activated lymphocytes, monocytes or macrophages. Beside many other stimulating or regulatory effects on various cell types one common feature of said IC is the upregulation of the expression of adhesion molecules—such as ICAM-1, VCAM-1, or ELAM-1—on the endothelial cell surface, which leads to an adhesion competent state of the cells. This adhesion competent state is defined as the period where a cell is competent to adhere to other cells or to an extracellular matrix. A well-known example is the increased adhesion of activated leukocytes to the endothelium. Additionally, it is described that IL-1β, IFN-γ and TNF-α exert an anti-proliferative effect on endothelial cells. Moreover, IFN-γ and TNF-α have even been shown to induce apoptosis in endothelial cells in vitro.

By contrast the AGFs, such as VEGF and bFGF, function as potent mitogens and chemotactic factors for endothelial cells. bFGF is a pleiotropic factor that has been found in almost all normal tissues and has a broad specificity for a number of target cells. Moreover, bFGF was shown to induce angiogenesis in vitro and in vivo. VEGF is a secreted protein that shows a high specificity for endothelial cells and promotes angiogenesis during normal physiological processes. Furthermore, VEGF strongly induces microvascular permeability that is also a general feature of tumor-associated microvasculature. Several lines of evidences suggest that VEGF and bFGF which display synergistic effects in the induction of angiogenesis in vitro and in a mouse model in vivo might contribute to the pathological process of tumor-associated angiogenesis (Plate et al., 1992, *Nature* 359, 845–848).

Considering that activation of endothelial cells plays a critical role in many physiological adaptations or pathological dysfunctions such as inflammation, haemostasis, immune reactions, psoriasis, atheriosclerosis, wound healing, angiogenesis or neovascularisation e.g. of malignant tumors (*Cotran & Pober*, 1988, *Endothelial activation: its role in inflammatory and immune reactions. In endothelial cell biology*, N. Simionescu and M. Simionescu, eds. (New York: Plenum Press), pp. 335–347) there is a high need to understand, influence and control the different stages of activation of endothelial cells. Additionally, a clear determination of the different phenotypes of endothelial cells is of particular interest for a decision on a proper therapeutic strategy, which can provide relief for a patient suffering from the medical syndromes adjacent to the activation of endothelial cells as mentioned above.

SUMMARY OF THE INVENTION

Thus, it is an object of the present invention to provide means to induce or repress the development of different stages of cell activation, specifically of endothelial cells. Additionally, it is an object of the invention to provide a method for the determination of the stage of cellular differentiation. Furthermore, it is an object of the present invention to provide means and methods, respectively, for modifying the differentiation and/or proliferation of cells, e.g. of tumor cells, which are also useful for treatment of diseases.

The invention, inter alia, comprises the following, alone or in combination: an eukaryotic expression vector comprising a nucleic acid sequence encoding the Guanylate Binding Protein-1 gene (GBP-1) or a functional part thereof; a vector comprising a nucleic acid sequence encoding the GBP-1 gene or a functional part thereof wherein said nucleic sequence is fused with a gene coding for a shuttle protein; the vector as above, wherein said vector is eukaryotic; the vector as above, wherein said shuttle protein is specific for endothelial cells; the vector as above, wherein said shuttle protein is HIV-1-Tat; the vector as above, wherein the nucleic acid sequence coding for GBP-1 or a part thereof is inserted in said vector in antisense orientation; the vector as above, wherein said nucleic acid sequence is under the transcriptional control of a homologous element regulating the expression of a normal GBP-1 gene; the vector as above, wherein said nucleic acid sequence is under the transcriptional control of a heterologous promoter; the vector as above, wherein said promoter is a constitutive, inducible and/or cell-type-restricted promoter; the vector as above, wherein said vector comprises one or more genes coding for a substance inducing and/or enhancing GBP-1 gene expression; the vector as above, wherein the gene is a cytokine gene; the vector as above, wherein said vector is a viral vector; the vector as above, wherein said viral vector is a retroviral vector; the vector as above, wherein said retroviral vector is replication defective; a producer cell comprising a viral vector as above and a DNA construct coding for proteins required for said viral vector to be packaged;

a viral particle comprising the retroviral vector as above;
the viral particle as above obtainable by the producer cell as above;
a retroviral provirus obtainable by infection of target cells with the retroviral particle as above;
a mRNA of the retroviral provirus as above;
a RNA of the vector as above;
a cDNA of the RNA as above;
a recombinant protein with functional properties of GBP-1;
the protein as above linked with a shuttle protein;
the protein as above, wherein the shuttle protein is specific for endothelial cells;
the protein as above wherein the shuttle protein is HIV-1-tat;
an antibody directed against GBP-1 or parts thereof;
an antibody directed against the GBP-1 antibodies as above;
use of antibodies as above for the detection/quantification of GBP-1 expression;
a cell transduced with the vector as above and/or infected with a viral particle as above;
the cell as above, wherein said cell is an endothelial cell;
a method for introducing a nucleic acid sequence encoding the GBP-1 gene or a functional part thereof in sense or antisense orientation into cells comprising transfection of a cell or organism with said nucleic acid sequence, with RNA of said nucleic acid sequence, with the vector as above or infection said cell or organism with the recombinant viral particle as above;
a method for producing recombinant GBP-1 protein comprising: (a) transduction of a cell or organism with the vector as above and/or infection with a viral particle as above, (b) cultivation of said cell or organism, and (c) isolation of the recombinant GBP-1 protein or the functional part thereof;
an oligonucleotide hybridizing under stringent conditions to a nucleic acid sequence encoding the GBP-1 gene, a part thereof and/or a regulatory element thereof;
the oligonucleotide as above selected from a group consisting of oligonucleotides with the sequence according to SEQ ID NO.: 1 to SEQ ID NO.: 5;
use of the oligonucleotides as above for the detection and/or quantification of the GBP-1 gene expression in vitro or in vivo;
a diagnostic component comprising the oligonucleotides as above;
a diagnostic kit comprising a diagnostic component as above;
a method for determination of the stage of cellular differentiation in cells, wherein GBP-1 gene expression is used as a marker for activating substances inhibiting cell proliferation and/or increasing adhesion competence of cells;
a method for modulation of GBP-1 gene expression and/or GBP-1 protein activity in cells, comprising addition of a substance inducing, enhancing or repressing GBP-1 gene expression and/or enhancing or inhibiting GBP-1 protein activity in said cells;
the method as above, wherein the vector as above, the producer cell as above, the viral particle as above, the RNA as above, one or more oligonucleotides as above, a cytokine and/or a growth factor are added;
use of the method as above for the modulation of cell differentiation;
use of the method as above for inhibition of viral replication of virus-infected cells comprising inducing the GBP-1 gene expression and/or enhancing the GBP-1 protein activity;
a method of cultivation of eukaryotic cells comprising addition of the vector as above, the viral particle as above, the RNA as above, oligonucleotides as above, and/or the addition of an inducer or repressor of GBP-1 gene expression or protein activity to the cell culture medium, and culturing the cells under suitable conditions;
a GBP-1 gene, a functional part thereof, a protein with functional properties of GBP-1 as above, GBP-1 antibodies as above, anti-GBP-1 antibodies as above, the vector as above, the producer cell as above, the viral particle as above, the RNA as above and/or the oligonucleotides as above for the use as inhibitor of rejection of transplanted organs, for use in the treatment of malignant disease and/or for the treatment of any other relevant disease or disorder;
use of a GBP-1 gene, a functional part thereof, a protein with functional properties of GBP-1 as above, an inducer or repressor of GBP-1 gene or protein activity, GBP-1 antibodies as above, anti-GBP-1 antibodies as above, the vector as above, the producer cell as above, the viral particle as above, the RNA as above and/or the oligonucleotides as above for producing a medicament for gene therapy, for the inhibition of rejection of transplanted organs, for the treatment of malignant disease and/or for the treatment of any other relevant disease or disorder;
a vaccine comprising the GBP-1 gene, a functional part thereof, a protein with functional properties of GBP-1 as above, GBP-1 antibodies as above, anti-GBP-1 antibodies as above, the vector as above, the producer cell as above, the viral particle as above, the RNA as above and/or the oligonucleotides as above;
a method for inhibition of rejection of transplanted organs, of treating malignant disease or any other relevant disease or disorder comprising administering to a subject in need a therapeutically effective amount of a GBP-1 gene, a functional part thereof, a protein with functional properties of GBP-1 as above, GBP-1 antibodies as above, anti-GBP-1 antibodies as above, an inducer or repressor of GBP-1 protein activity, the vector as above, the producer cell as above, the viral particle as above, the RNA as above and/or the oligonucleotides as above;
a pharmaceutical composition comprising a therapeutically effective amount of a GBP-1 gene, a functional part thereof, a protein with functional properties of GBP-1 as above, GBP-1 antibodies as above, anti-GBP-1 antibodies as above, an inducer or repressor of GBP-1 protein activity, the vector as above, the producer cell as above, the viral particle as above, the RNA as above and/or the oligonucleotides as above and a pharmaceutical acceptable carrier or diluent.

DETAILED DESCRIPTION OF THE INVENTION

While extensively studying the different states of activation of endothelial cells the inventors of the present invention identified a gene which is mutually exclusively expressed in the different phenotypes of endothelial cells. This gene was identified as the Guanylate Binding Protein 1 (GBP-1) gene. The GBP-1 protein was originally discovered in vitro as an abundant interferon-inducible protein in human or mouse fibroblasts (Cheng et al., 1983, *J. Biol. Chem.*, 258:7746–7750) that was retained on guanylate agarose affinity columns. Thereafter, GBP-1 was identified as the first member of a distinct family of GTP-binding proteins, the GBPs (Cheng et al., *Mol. Cell Bio.*, 11:4717–4725, 1991) which are strongly inducible by interferon (IFN). A CaaX motif at the C-terminus of human GBP-1 serves as an isoprenylation signal, allowing the addition of a 20-carbon molecule that serves to anchor the protein to a membrane (Schwemmle et al., 1994, *J. Biol. Chem.* 269: 11299–11305). The physiological role of GBP-1 remained unknown until now.

Figure 2:
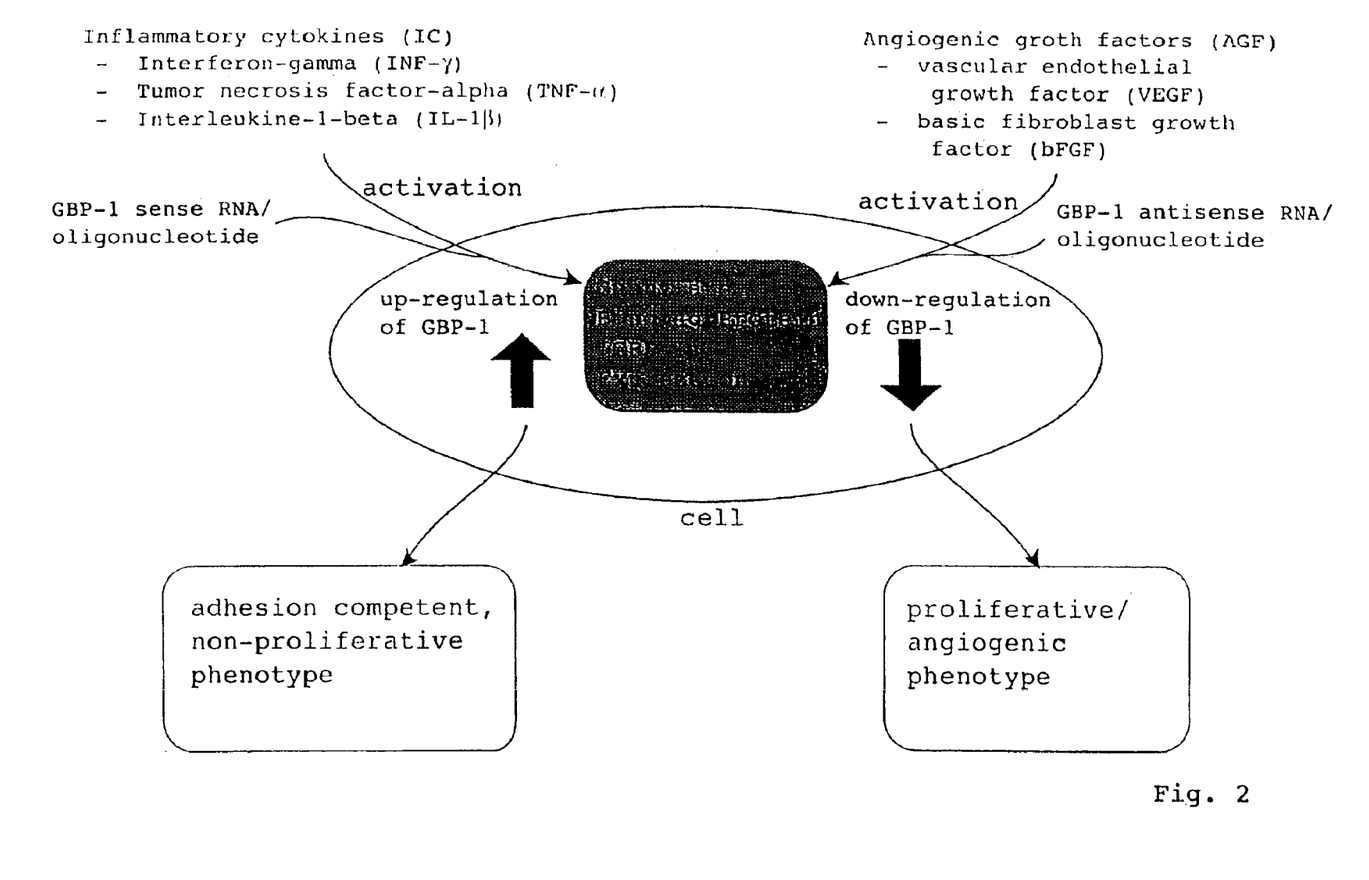
FIG. 2 is a schematic showing a biological function of GBP-1 gene expression.

The protein encoded by the GBP-1 gene is now identified as the cellular factor inducing the differentiation of at least two known phenotypes of activated endothelial cells. The inventors describe and proof here for the first time a biological function regarding GBP-1 gene expression (FIG. 2). Thus, it was shown that at the molecular level of the two different stages of activation or phenotypes of endothelial cells, respectively, the GBP-1 expression is clearly distinguishable and mutually exclusive. Accordingly, the differentiation to motility and cell proliferation characteristic of the angiogenic phenotype of endothelial cells is due to a down-regulation of the GBP-1 gene expression by AGF. On the other hand it was shown that an increasing expression of GBP-1 gene product is due to an induction by IC and that increased expression of GBP-1 induces the differentiation of an adhesion-competent and non-proliferative endothelial phenotype. The inventors provide evidence that the whole group of inflammatory cytokines and not only some members like IFN-γ induce the adhesion-competent and non-proliferative phenotype. This is especially surprising for endothelial cells since the action of cytokines is preferably studied for cells of the immune system. The detailed understanding of the molecular and cellular events in endothelial cell activation induced by GBP-1 is necessary for the development of therapeutics and diagnostics interfering with regulation and differentiation of cells, preferably endothelial cells.

Accordingly, the present invention provides an expression vector preferentially for eukaryotic cells comprising a nucleic acid sequence encoding the Guanylate Binding Protein-i gene (GBP-1) or a functional part thereof. It has to be understood that in the context of the present invention the "GBP-1 gene" as used herein refers to all nucleotide sequences coding for a functional form of the GBP-1 protein or parts thereof and include especially naturally occurring variants of the human GBP-1 gene.

After infection or transfection of an eukaryotic target cell with said vector the GBP-1 gene is expressed in the cell. Due to this introduction of the vector expressing the GBP-1 gene or functional parts thereof the intracellular amount of GBP-1 gene product is increased. Surprisingly, it was shown that by increasing the amount of intracellular GBP-1 the differentiation of endothelial cells in direction to an adhesion-competent and/or non-proliferative endothelial phenotype is induced. The enhanced expression of the GBP-1 gene or functional parts thereof in said cells results in a reduction of proliferation activity and/or an increase of cell-to-cell adhesion. The prefered target cells transduced with the vector are endothelial cells, especially, endothelial cells involved in neovascularization and in the recruitment of inflammatory cells into tissues. Surprisingly, it was also shown that an enhanced expression of GBP-1 gene in non-endothelial cells also induces a non-proliferative phenotype. This is, e.g., the case in inflammatory and immune cells, such as monocytes or lymphocytes, but also in other cell types. Accordingly, with the directed induction of said phenotypical changes by the introduction of the vector according to the present invention particularly pathological dysfunctions such as cancer, sarcoma, lymphoma, hemangioma, artherosclerosis or restenosis can be treated, since the reduction of proliferation and/or increase of cell-to-cell adhesion moderate these symptoms.

Additionally, the vector according to the present invention can be introduced in cell lines, preferably fibroblast, which are used as "feeder-cells" for the cultivation of complex or any other relevant cells. When complex cell types, e.g. Keratinocytes, are cultivated in vitro they must be provided (fed) with a still unknown combination of factors. In the case of cultivation of Keratinocytes said factors are provided by fibroblasts, the so-called feeder-cells, which are co-cultivated. However, co-cultivation has the disadvantage that fibroblasts, which have a much higher growth rate, sooner or later simply overgrow the Keratinocytes. Thus, fibroblasts, which are used as feeder-cells are normally treated with a highly toxic cytostaticum (Mitomycin C) to obtain growth arrest. Accordingly, also co-cultivated Keratinocytes get in contact with small concentrations of the cytostaticum. Nevertheless, such contact must be avoided when cultivated Keratinocytes are used for therapeutical purposes. According to the present invention the vector comprising the GBP-1 gene, the GBP-1 RNA or viral particles comprising the GBP-1 gene is introduced into feeder-cells such as fibroblasts. Subsequently, GBP-1 expression is enhanced and accordingly, the growth of said transduced cells is reduced. Thus, the fibroblasts or any other feeder-cell lines can be growth arrested without using any cytostatic toxins.

According to a further embodiment of the present invention the nucleic acid sequence encoding the Guanylate Binding Protein-1 gene or parts thereof are inserted in antisense direction into the vector. Expression of these antisense constructs leads to RNA molecules that hybridize to the normal GBP-1 mRNA in a cell. This hybridization interferes and/or inhibits the translation of the GBP-1 mRNA to GBP-1 protein of said cell. Consequently, no GBP-1 protein is and can be synthesized. Accordingly, due to this down-regualtion of expression of GBP-1 protein a so-called "counter effect", comprising a repression of the adhesion competent state and an activation of cell proliferation, is induced.

On one hand the introduction of said vector can be used to repress the IC-induced upregulation of adhesion molecules. Thus, the adhesion competence of cells transduced with the vector according to the invention can be reduced. This repression of cell-to-cell adhesion is preferably used to avoid undesirable immune reactions, such as allergic reactions and/or a rejection of transplanted tissue or organs.

Furthermore, the expression of said antisense construct can also be used to down-regulate the GBP-1 expression in endothelial cells of Kaposi's sarcoma, since in vivo biopsy of Kaposi's sarcoma showed an increased level of GPB-1. This down-regulation of GBP-1 expression reduces the adhesion competence of the endothelial cells, thereby avoiding the immigration of additional immune cells into the Kaposi's sarcoma. Since normally said immigration is responsible for the fast and extensive growth of Kaposi's sarcoma, the down-regulation of GBP-1 expression reducing said immigration can be applied to avoid further spread of the disease in a patient.

In addition, the introduction of a vector comprising the antisense construct according to the present invention can be used to potently protect cells from an IC-induced inhibition of cell growth. Thus, said introduction, but also the simple addition of GPB-1 antisense constructs to cells result in an induction or increase of cell proliferation. Accordingly, the present invention provides means to activate and/or increase the proliferation of cells in culture such as cell lines, primary cells or any other relevant cells. This activation is especially useful for a fast and controllable expansion of cells in vitro. Considering industrial use of an acceleration of the expansion of cells of only 10% reduces cost for cell culture dramatically.

The expression of the nucleic acid sequence encoding the GBP-1 or parts thereof is according to one embodiment of the present invention under the transcriptional control of the normal (homologous) cellular sequence regulating the expression of a normal GBP-1 gene. The use of the normal regulatory elements may be especially important, if the vector carrying the GBP-1 gene is used for gene therapy. Normally, methods of gene therapy comprise the replacement of a non-functional gene with a corresponding functional gene. For this replacement it is highly desirable that the newly introduced gene is under the same physiological control as the natural gene. Thus, in case that the GBP-1 gene is used for gene therapy it is preferably under transcriptional control of its normal promoter. Accordingly, the newly introduced GBP-1 gene is under the same physiological control as a natural GBP-1 gene. Due to the replacement of the non-functional with a functional GBP-1 gene the physiological task of the GBP-1 gene can be restored.

Furthermore, according to another embodiment of the invention, the homologous regulatory elements of the GBP-1 gene are, used in vectors comprising the antisense information of the GBP-1 gene or parts thereof. Accordingly, after introduction of the vector in a cell the expression of the antisense GBP-1 RNA is regulated by the same control mechanisms as the normal GBP-1 gene expression. Thus, the amount of antisense GBP-1 RNA expressed in said cell corresponds to the amount of expressed GBP-1 RNA. In this case the equal amount of GBP-1 antisense RNA efficiently neutralizes the GBP-1 RNA by hybridizing to said RNA. This hybridization essentially interferes with the binding of the GBP-1 RNA to the ribosome for protein synthesis. Thus, said interference results in an interruption or termination of the translation of the GBP-1 RNA into protein. Accordingly, no further GBP-1 RNA protein can be synthesized and the cell remains no longer in the state of the activated but non-proliferative phenotype. Instead, said cells switch to an inactivated state or are further pushed into the direction of the proliferating phenotype.

However, the main advantage of the homologous regulatory element is that the expression of antisense GBP-1 is influenced in the same manner as the expression of sense GBP-1 by different stimulating factors of the cell: In case of an IC stimulus, the expression of both, GBP-1 antisense RNA and GBP-1 RNA is upregulated, while in case of an AGF stimulus the GBP-1 RNA expression as well as the GBP-1 antisense RNA expression is downregulated. Accordingly, undesired side effects, which might be due to an overexpression of the GBP-1 antisense RNA at a time point where no GBP-1 RNA is present in the cell can be minimized.

Alternatively, according to another embodiment the nucleic acid sequence encoding the GBP-1 or parts thereof—either in sense or antisense orientation—is under the transcriptional control of a heterologous promoter. The term "heterologous" is used, hereinafter, for any combination of DNA sequences that is not normally found intimately associated in nature. According to the present invention the heterologous promoter can be an enhancer element or any other promoter enhancing gene expression. According to a further embodiment of the present invention, heterologous promoters are constitutive, inducible and/or cell-type-restricted promoters that promote the expression of the GBP-1 gene or parts thereof in a host organism. Constitutive promoters are constantly expressed in a cell. Since they are often derived from regulatory element of a cellular housekeeping gene or a structural gene of a virus, they are quite insensitive to most inhibiting or activating stimuli. In contrast to constitutive promoters, inducible promoters are strictly regulated and only active in the presence of the appropriate inducer molecule. The advantage of an inducible promoter is the controllable activation of the gene expression by externally provided inducer or repressor molecules. Also a cell-type-restricted promoter can be understood as inducible promoter. In this case said promoter can be activated by internal inducer or repressor molecules, which are provided by the distinct cell type. Thus, said promoters are only active in said distinct cell type, while in all other cells the transcription of said promoters is prevented or at least reduced.

A heterologous promoter is used to overexpress the GBP-1 gene, functional parts thereof or antisense transcripts in the transduced cell. The overexpression of the GBP-1 antisense transcription from a heterologous promoter results in high amounts of antisense RNA with in the cell. This antisense RNA competitively binds to the cellular GBP-1 RNA and thus, inhibits translation of the cellular GBP-1 RNA into protein. The inhibition of translation results in a prompt and complete inhibition of the adhesion competent, non-profiveative phenotype and, consequently, in a prompt induction of cell proliferation. The up-regulation of cell proliferation improves e.g. healing of wounds and of freezing or burning injuries. Simultaneously, the inhibition of the adhesion competence of cells avoid the recruitment of immune cells, which could lead to further irritation or inflammation e.g. in the case of inflammatory diseases like chronic ulcerative diseases, psoriasis or Morbus Crohn. Accordingly, the introduction of the vector comprising and overexpressing the GBP-1 gene or parts thereof in antisense orientation are specifically useful for the treatment of inflammatory diseases as well as for wound healing and other comparable diseases.

Overexpression of the GBP-1 gene in sense orientation is especially useful to stop the proliferation of uncontrolled growing cells, such as in malignant tumors, carcinomas or lymphomas, but is also useful to avoid further recruitment of cells inducing tumorangiogenesis.

According to another embodiment of the present invention the vector comprises at least one gene encoding a substance inducing and/or enhancing GBP-1 gene expression. For inducing and/or enhancing the GBP-1 gene expression said substances activate the regulatory elements controlling the GBP-1 gene expression. Thus, the gene inserted in the vector, which encodes a substance inducing and/or enhancing GBP-1 gene expression may be dependent on the regulatory elements or promoter controlling GBP-1 gene expression: The homologous promoter controlling the normal cellular GBP-1 gene expression can, for example, be induced by cytokines. In case that the GBP-1 gene of the expression vector according to the present invention is under transcriptional control of the normal, homologous promoter, said carries in a preferred embodiment of the invention in addition at least one cytokine gene, such as the interleukine, tumor necrosis factor or interferon gene. Hence, the expression of said cytokine gene induces or further enhances the expression of the GBP-1 gene, functional parts thereof or corresponding antisense orientated sequences.

Furthermore, when an inducible promoter is used for the trancriptional control of the GBP-1 gene expression the vector according to the present invention carries the gene encoding the inducer molecule correspondent to the inducible promoter. Accordingly, in the case where a cell-type-restricted promoter is used the vector according to the present invention carries the gene encoding the limiting cell-specific factor, which induces and/or enhances the cell-type-restricted promoter.

In a further embodiment of the present invention the expression vector encoding the GBP-1 gene or parts thereof—either in sense or antisense orientation—is a viral vector. Accordingly, said viral vector represents every recombinant viral vector e.g. adenoviral, retroviral, poxvirus, herpes virus or adeno-associated virus vectors, which can be used for the transfer of heterologous genetic information into a cell. Therefore, said viral vector comprises all genes and factors, which will be needed for said transfer of the heterologous genetic information into a target cell.

According to a preferred embodiment of the present invention the viral vector is based on a retrovirus. Retroviruses or retroviral vectors are ideal vehicles for the transport of genetic information into a target cell in vivo and in vitro. Firstly, retroviruses or retroviral vector systems are well studied and therefore, nowadays the preferred system for gene therapy. Secondly, retroviral vectors are easy to handle or to modulate. For the construction of a recombinant retroviral vector a DNA plasmid is prepared according to standard protocols to carry the desired genetic information and essential genes of the retroviral genome. After transfecting a cell with said DNA vector the retroviral RNA genome is transcribed and packaged into an infectious replication competent particle. Said particle is isolated from the supernatant of the cells and used for infecting a target cell in vivo or in vitro. Immediately after infection the retroviral RNA genome is reverse transcribed into a DNA copy, which subsequently is stably integrated into the cellular genome.

However, aspects of safety have to be considered, since the stable integration of the retroviral genome into the genome of the target cell bears the risk of genomic rearrangements or dysregulation of cellular factors, including proto-oncogenes. Even if the chances are quite small, it is accepted that said risk increases with the number of infection events. Thus, according to a further embodiment of the present invention the retroviral vector is replication-defective. The genome of a replication-defective retroviral vector lacks the genetic information of one or more of the proteins required for particle formation. Thus, according to a further embodiment of the present invention a producer cell encoding and expressing all proteins required for particle formation and packaging of said vector is provided.

In accordance with said producer cell for retroviral particles, the present invention further provides producer cells for other viral vectors, such as adenoviral, adeno-associated or herpesviral vectors. Said cells provide all proteins essential for particle formation of said viral vectors. Said viral particles are isolated from the supernatant of said cells.

According to still a further embodiment of the present invention, viral particles comprising the viral vector according to the present invention and/or isolated from the supernatant of said producer cell are provided. Retroviral particles as well as other viral particles are used to infect cells either in vivo or in vitro.

Furthermore, the present invention provides the retroviral provirus, which is the integrated DNA copy of the retroviral vector and which is transcribed into mRNA like any other naturally occurring gene. Thus, the present invention also provides the mRNA corresponding to the retroviral provirus, the RNA and cDNA of the viral vectors as described above and the cell transduced with said viral vectors and/or infected with said retroviral or viral particles, respectively. Additionally, said cell is according to a still further embodiment of the present invention an endothelial cell, but can also be every other cell as, e.g., an immune cell.

According to the present invention a method for introduction of the nucleic acid sequence encoding GBP-1 gene or parts thereof in sense or antisense orientation into cells in vivo or in vitro is provided. This method comprises, inter alia, transfection of a cell or organism with the vectors or the RNA according to the present invention or infection of said cells or organisms with the viral particles. To increase the amount of efficiently transduced cells the transfected or infected cells can be put under selection pressure.

Additionally, the present invention provides a method for producing recombinant GBP-1 protein. For the production e.g. in eukaryotic cells these cells are transduced with an eukaryotic vector encoding the GBP-1 gene or parts thereof and/or infected with a viral particle which codes for the GBP-1 gene or parts thereof. Said cells are cultivated under suitable conditions until the recombinant GBP-1 protein or parts thereof are isolated. This method allows a reasonable priced production of large amounts of recombinant GBP-1 protein or parts thereof, which can be used as a vaccine or for the treatment of a proliferative disorder of cells. If the pure GBP-1 protein is administered extracellularly to cells it is probably not able to cross cell membranes and therefor can not enter the cytoplasm and/or the nucleus of the cell. Thus, in a preferred embodiment of the present invention said method is used to produce a fusion protein of the GBP-1 protein and a so-called "shuttle protein". It has been found that shuttle proteins—extracellularly administered—are able to enter the cytoplasm and/or the nucleus. Accordingly, also GBP-1 protein will be able to enter the cell if it is fused to such a shuttle protein. In a preferred embodiment the HIV1-tat gene is fused to the GBP-1 gene since it has been shown that HIV1-tat specifically enters cells comprising $\alpha V\beta 3$ molecules on their surface. Said molecules are, inter alia, expressed on activated endothelial cells as well as on cells of proliferating tumors. Accordingly, uptake of GBP-1-HIV1-tat fusion protein into said cells is facilitated.

The recombinant GBP-1 protein can also be produced in prokaryotic cells. In this case the GBP-1 gene is introduced in a prokaryotic expression vector and prokaryotic cells e.g. of Escherichia coli are transformed with said vector. Afterwards, the recombinant GBP-1 protein can be extracted. As already described in the paragraph above for the eukaryotic expression systems the GBP-1 protein is preferentially produced as a fusion protein linked with an appropriate shuttle protein.

As described in the paragraphs above the present invention provides an expression vector comprising the GBP-1 gene or parts thereof—either in sense or antisense orientation—fused in frame to the nucleic acid sequences encoding a shuttle protein. This vector can, thus, be used to produce the recombinant GBP-1 fusion protein as mentioned above according to the method as mentioned above.

Additionally, the present invention provides oligonucleotides hybridizing under stringent conditions in sense or antisense orientation to a nucleic acid sequence encoding the GBP-1 gene, a part thereof or the regulatory elements thereof. The term "under stringent conditions" defines parameters according to standard protocols, such as reaction temperature, allowing hybridization of DNA-DNA and/or DNA-RNA sequences with a homology about and above 70%. Generally, oligonucleotides can be prepared by digesting DNA or are chemically, enzymatically or in vitro synthesized nucleic acid sequences, such as RNA or DNA, which are complementary to a target nucleic acid sequence. The length of an oligonucleotide is variable and depends primarily on the melting temperature of the selected sequence. If the melting temperature of an oligonucleotide according to the present invention would fall under 35° C. the length of the oligonucleotide must be prolonged. Furthermore, the oligonucleotides according to the present invention can be modified DNA or RNA molecules synthesized by using modified nucleotides, such as e.g., desoxy-, phosphothioester- or methoxy-modified nucleotides.

In a preferred embodiment of the present invention oligonucleotides are provided, hybridizing in sense or antisense orientation to the GBP-1 gene and/or its regulatory elements. Said oligonucleotides are preferably selected from the following nucleotide sequence 5'-CTT TTT CTC CTT AGT TCA CG-3' (SEQ ID NO.: 1),5'-TCC CTT GTC TGT TCT TTT TC-'3 (SEQ ID NO.: 2), 5'-TCC CTT GTC TGT TCT TTT TCT CCT TAG TTC ACG-'3 (SEQ I) NO.: 3), 5'-GCT CTA GAT TAG CTT ATG GTA CAT GCC TTT CG-3' (SEQ ID NO.: 4) or 5'-CGG AAT TCG CCG CCA TGG CAT CAG AGA TCC ACA TG-3' (SEQ ID NO.: 5). Said oligonucleotides are used as primers for a PCR or RT-PCR to amplify defined parts of the GBP-1 gene or gene product, respectively. Accordingly, such oligonucleotides are especially useful for a very sensitive detection and/or quantification of GBP-1 gene or gene products in cell culture or in tissue samples. Alternatively, said oligonucleotides are used as probes for the detection and/or quantification of GBP-1 specific mRNA in a Northern Blot assay, in-situ hybridization, S1-nuclease mapping or similar techniques.

The invention further provides a diagnostic component comprising as reactive component the oligonucleotide as described above in an aqueous medium in a quantity effective to form complexes in a technique as described above or any other relevant diagnostic assay. These complexes are e.g. hybridization-complexes between a nucleic acid sequence derived from a biological sample and the reactive component.

Additionally, the present invention provides a kit for a diagnostic assay comprising said diagnostic component in a suitable container and/or attached to a solid support. Since the diagnostic reagent is attached to a solid support, the risk is minimized to loose any complexes formed between the diagnostic reagent and GBP-1 RNA or protein derived from a biological sample before they have been detected or quantified.

Additionally, according to a further embodiment of the present invention the oligonucleotides as described above can be used for the modulation of the GBP-1 gene expression in vivo or in vitro. Thus, the oligonucleotides enter the cell and get to the nucleus of the cell, where they bind to specific sequences of the GBP-1 gene e.g. the splice donor or acceptor sites and thus, interfere and/or inhibit GBP-1 gene expression. Alternatively, said oligonucleotides bind to GBP-1 specific RNA and inhibit translation of said RNA, thus inhibiting GBP-1 protein synthesis.

Additionally, the present invention provides a method for determination of the stage of cellular differentiation in cells, wherein GBP-1 gene expression is used as a marker for activating substances inhibiting gene cell proliferation and/or increasing adhesion competence of cells. It was shown by the inventors that in endothelial cells the expression of GBP-1 is unique in that it is rapidly induced by three inflammatory cytokines—interleukine, tumor necrosis factor, interferon and/or any functional analogue—and is down-regulated by the AGF's, namely VEGF and bFGF and/or any functional analogue. Therefore, the method, described above, provides for the first time a common and specific molecular marker for endothelial cells activated by inflammatory cytokines and/or down-regulated by angiogenic growth factors. According to said method the expression of the GBP-1 gene in cells of a tissue under investigation is analyzed using oligonucleotides to detect and/or quantify GBP-1 mRNA or fragments thereof in a RT-PCR, Northern blot hybridization, in-situ hybridization or any other relevant technique.

Alternatively, also labeled RNA complementary to GBP-1 mRNA and synthesized by in vitro transcription can be used for the detection of GBP-1 mRNA according to the method of the present invention. For this in vitro transcription the present invention also includes a vector, wherein the GBP-1 cDNA for synthesis of GBP-1 sense and antisense RNA is under the control of, inter alia, a T7, T3, SP6 promoters and, thus, can be transcribed in vitro by T7, T3, SP6 polymerases.

The detection of GBP-1 expression in cells according to the method of the present invention indicates that said cells are activated by inflammatory cytokines. Furthermore, the detection of GBP-1 expression also indicates that the cells are in an adhesion competent state.

The detection of no GBP-1 expression indicates that the cell is not in an adhesion competent state, which is for example a proliferation competent state. The molecular mechanism underlying down-regulation of GBP-1 expression by VEGF and/or bFGF remains unknown. The method is especially useful to determine early changes in the state of adherence of cells. According to a further embodiment of the present invention this method is used preferably for said determination of the activation state—adhesion competent versus proliferative—of tissues, preferably in endothelial cells, during development, disease or as follow-up of a medical therapy.

According to the present invention the method for determination of the stage of cellular differentiation can also be used to detect and/or quantify the GBP-1 protein or fragments thereof using inter alia GBP-1 antibodies in a Western Blot assay, immunohistochemistry or an ELISA.

The invention further provides a method for the modulation of GBP-1 gene expression in cells, especially endothelial cells, in vivo or in vitro. For this, a substance either inducing or repressing GBP-1 gene expression is added. According to a preferred embodiment of the present invention at least one cytokine, preferably interleukine, tumor necrosis factor and/or interferon, is added to induce and increase GBP-1 gene expression. Said GBP-1 gene expression is then used for the inhibition of cell proliferation and/or for increasing the adhesion competence of cells.

On the other hand to reduce GBP-1 gene expression at least one growth factor preferably VEGF and bFGF is added. The inventors showed that both the GBP-1 expression and the IL-1β and IFN-γ biological activities in endothelial cells were down-regulated by the angiogenic growth factors VEGF and bFGF. Moreover, long term pre-treatment of said endothelial cells with VEGF and bFGF fast abolished the expression of GBP-1 as well as the ability to bind monocytes induced by Il-1β. This down-regulation of GBP-1 gene expression is especially interesting for in vitro expansion of eukaryotic cell cultures, since it increases cellular proliferation and decreases cell-to-cell adhesion. Notably, said down-regulation is also very useful in vivo, especially during or after organ transplantation. Indeed, the rejection of a transplanted organ is avoided or at least postponed, if due to the inhibition of adhesion of immune cells to the endothelium of relevant blood vessels the recruitment of immune cells into the transplanted organ is inhibited.

Instead of modulating the GBP-1 gene expression the GBP-1 protein activity can be enhanced or reduced adding suitable substances. Such substances include molecules that inactivate the GTPase function of the GBP-1 protein and also intracellularly expressed GBP-1 antibodies.

This method for modulation of GBP-1 gene expression or protein activity can be used to influence the cell differentiation. It can be applied to inhibit viral replication, e.g. the replication of HIV, in vivo or in vitro. It is known that the state of cellular differentiation, especially activation of a non-proliferative phenotype, hinders the efficient viral replication in an infected cell. Thus, said method can be used to increase the GBP-1 gene expression or to enhance the GBP-1 protein activity with the goal to induce the non-proliferative phenotype of a cell. Hence, a virus infecting said cell can not replicate at all or less efficiently. With the reduction of viral replication in infected cells the amount of free virus in a patient is reduced. In case of an infection with HIV said reduction of the amount of free virus contributes to a later onset of the actual disease AIDS and/or at least to a prolonged symptom-free period for the patient.

The present invention also includes a method for cultivation of eukaryotic cells. This method is especially useful—as already described above—for the in vitro expansion of primary cells or any other cells or cell lines, where the cultivation or expansion in culture is difficult, time-consuming or cost-intensive. Alternatively, this method is also useful—as described above—to induce a growth arrest in cells in culture. According to the method of the present invention the cells in culture are incubated or transfected with an effective amount of a GBP-1 gene, functional parts thereof, GBP-1 protein, GBP-1 fusion protein as described above, GBP-1 RNA in sense or antisense either isolated or expressed from a vector of the present invention, oligonucleotides as described above, viral particles as described above, an inducer or inhibitor of GBP-1 gene expression, such as VEGF or bFGF, and/or and enhancer or repressor of GBP-1 protein activity, which can be added to the cell culture medium.

Furthermore, the present invention provides the GBP-1 gene, functional parts thereof, its sense or antisense RNA, GBP-1 antibodies, anti-GBP-1 antibodies, the GBP-1 protein or GBP-1 fusion protein as described above, the vectors as described above, the producer cell as described above, the viral particle as described above, the RNA as described above and/or the oligonucleotides as described above for the manufacture of a medicament, inter alia, for gene therapy, for the use as an inhibitor of rejection of transplanted organs and/or for the treatment of malignant disease, such as cancer, sarcoma, lymphoma, but also for the treatment of hemangioma, artherosclerosis, restenosis, inflammatory processes like chronic ulcerative diseases, psoriasis, insect bites, freezing or burning injuries, wound healing, Morbus Crohn and/or any other relevant disease or disorder.

Additionally, the present invention provides a method for inhibition of rejection of transplanted organs, of treating malignant disease or any other relevant disease or disorder comprising administering to a subject in need thereof a therapeutically effective amount of the GBP-1 gene, functional parts thereof, its sense or antisense RNA, GBP-1 antibodies, anti-GBP-1 antibodies, an inducer or repressor of GBP-1 protein activity, the GBP-1 protein or GBP-1 fusion protein as described above, the vectors as described above, the producer cell as described above, the viral particle as described above, the RNA as described above and/or the oligonucleotides as described above.

Furthermore, the present invention provides a pharmaceutical composition used in vivo or in vitro as a vaccine comprising as a first component a therapeutically effective amount of the GBP-1 gene, functional parts thereof, its sense or antisense RNA, GBP-1 antibodies, anti-GBP-1 antibodies, an inducer or repressor of GBP-1 protein activity, the GBP-1 protein or GBP-1 fusion protein as described above, the vectors as described above, the producer cell as described above, the viral particle as described above, the RNA as described above and/or the oligonucleotides as described above, and as a second component a pharmaceutical acceptable carrier, diluent, or transport molecule.

The detailed examples that follow are intended to contribute to a better understanding of the present invention. However, it is not intended to give the impression that the invention is confined to the subject-matter of the examples.

EXAMPLE 1

Characterization of the Biological Functions of GBP-1 Gene Product

1. Differential Display RT-PCR (DDRT-PCR) Identified GBP-1 as a Gene Induced by IL-1β but not by VEGF in Human Microvascular Endothelial Cells from the Dermis (HDMVEC).

Most of the endothelial cells involved in vascular physiological and pathological processes are of microvascular origin. Human primary dermal microvascular endothelial cells (HDMVEC) and human primary umbilical vein endothelial cells (HUVEC) were purchased by Clonetics (San Diego, Calif.) and cultured in endothelial basal medium (EBM, Clonetics) supplemented with 5% foetal bovine serum (FBS), bovine brain extract 12 mg/ml, human epidermal growth factor 10 ng/ml, hydrocortisone acetate 1 mg/ml, gentamycin 50 mg/ml, amphotericin 0.25 mg/ml (Clonetics), penicillin 100 U/ml, and streptomycin 100 mg/ml (Gibco BRL, Eggenstein, Germany). Cells were propagated in flasks coated with 0.01% collagen type I (PromoCell, Heidelberg, Germany). Medium was replaced every 2–3 days, and cells were split once a week at a 1:6 (HDMVEC) or 1:10 (HUVEC) ratio and used until passage eight (HDMVEC) or fourteen (HUVEC).

To identify genes specifically expressed in cytokine-activated endothelial cells, using DDRT-PCR we compared the pattern of gene expression in HDMVEC (Clonetics, San Diego, Calif.) stimulated with the angiogenic factor VEGF165 to that of HDMVEC stimulated by the inflammatory cytokine, IL-1β. For stimulation recombinant human VEGF165 was purchased from R&D system (R&D Systems, Minneapolis, Minn.), recombinant human IL-1 from Boehringer Mannheim (Mannheim, Germany). HDMVEC were cultivated with complete EBM/5% FBS medium (Clonetics) in 175 cm2 flasks (Greiner, Frickenhausen, Germany) until they reached 80% confluence. Then, after resting for 24 hours in low-serum medium EBM/0.5% FBS (Clonetics) they were stimulated with the two cytokines diluted into low-serum medium, at the respective concentrations.

Subsequently, the total cellular RNA isolated using the RNeasy kit (QIAGEN, Hilden, Germany), according to the manufacturer's instructions from HDMVEC, which have been incubated for 5 hours with or without VEGF165 (10 ng/ml) or IL-1β (20 U/ml) was submitted to differential display analysis. Therefore, 1 µg of DNAse-I treated RNA was used as template in three reverse transcription reactions containing one of the three different one-based anchored 5'-H-T11M-3' primers (where H is the HindIII restriction site and M may be G, C or A) (RNAimage, GenHunter Corporation, Brookline, Mass.). Briefly, in the presence of 1× RT buffer (Gibco), 20 µM dNTPs, and 5'-H-T11M-3' primer at 0.2 µM, each RNA sample was incubated as follows in a Perkin-Elmer's 9600 thermocycler (Perkin Elmer, Roche Molecular Systems Inc., Branchburg, N.J.): 5 min at 65° C., 5 min at 37° C., 60 min at 42° C., 5 min at 75° C. and the After 5 min at 42° C., 100 units of Superscript-II reverse transcriptase (Gibco), were added to each tube for the 55-min incubation left at 42° C. Subsequently, PCR amplification was performed on ⅕ of the RT reaction volume in the presence of 1× PCR buffer, 1.5 mM MgCl$_2$, one unit of AmpliTaq polymerase (Perkin-Elmer), 2 µM dNTPs, 0.2 µM upstream 10 mer-primer (5'-TCGATACAGG-3' (SEQ ID NO.: 6)), 0.2 µM of the corresponding 5'-H-T11M-3' primer and α-[$^{33}$P]dATP (Amersham, Little Chalfont, Buckinghamshire, UK) in the Perkin-Elmer thermocycler 9600 device as follows: 5 min at 95° C., then 40 cycles: 30 sec at 94° C., 2 min at 42° C., 30 and finally 5 min at 72° C. 5 ml of the PCR reaction were loaded onto a 6% sequencing gel. The gel was blotted on a 3M Whatman paper, dried under vacuum at 80° C. and exposed overnight to an X-ray film (Amersham). The gel slices along with the 3M paper containing the bands of interest were cut out, and boiled 15 min in 100 ml H$_2$O. The DNA was then precipitated and used as a template in a cold PCR reaction performed as described for DDRT-PCR, except that the dNTPs concentration was increased to 20 µM and the radioactive nucleotides omitted. The reamplified fragments were directly radioactively labeled by random prime labeling (High Prime, Boehringer Mannheim) and used as a probe for Northern blot analysis. The PCR fragments of interest were cloned itno the pBlueSpript II+/− derived vector, pCRScript (Stratagene, Heidelberg, Germany) as described in the manufacturer's instructions. Cycle sequencing was performed using the fluorescent method ABI Prism (Perkin Elmer Applied Biosytems, Foster City, Calif.).

The pattern obtained with this primer combination (5'-HT11G-3' and TCGATACAGG (SEQ ID NO.: 6)) revealed the presence of a 330 bp differentially displayed product specifically upregulated in IL-1β-treated HDMVEC but not in VEGF165-treated or in non-treated control cells. The differential expression was confirmed by Northern blot hybridization on the corresponding RNAs using the radiolabeled 330 bp cDNA as a probe. Cloning and sequencing revealed that the differential display product matched the nucleotides 1430 to 1768 at the 3' end of the coding sequence of the human Guanylate Binding Protein-1 (GBP-1) 2.8 kb mRNA. GBP-1 is a GTPase of 67 kDa without any associated biological function, but that was interestingly discovered as an interferon-inducible protein in fibroblasts (Cheng et al., 1983), interferon-gamma belonging to the group of inflammatory cytokines. In these cells, GBP-1 can be induced by both a and y interferon but through different pathways, giving rise to different patterns of induction.

2. Dose Dependency and Time Course of GBP-1 mRNA Levels in Response to IL-1 β Stimulation.

Since this is the first report that GBP-1 gene expression is inducible by IL-1 β in HDMVEC, the inventors further characterized the induction by a time course and dose analysis. As little as 2 U/ml of IL-1β in the incubation medium resulted in a 2.4-fold increase in the GBP-1 mRNA level after 5 hours of treatment. Maximal induction (between 5-and 70-fold) was reached when 20 U/ml of IL-1β was used. Time course analysis revealed that the induction of GBP-1 mRNA was rapid, reached a maximum after 5 hours and remained at a high level over a period of 24 hours. IL-1β generated a rapid and stable intracellular signal leading to a GBP-1 kinetics of induction similar to that produced by IFN-γ in diploid fibroblasts or HeLa cells (Decker et al, 1991, Lew et al., 1991). Such high levels of expression, rapidly inducible, indicated that GBP-1 gene product plays a critical role in endothelial cell activation.

3. Effect of Cycloheximide on IL-1β Induction of the GBP-1 mRNA.

The rapid response of the GBP-1 gene to IL-1β suggested that in HDMVEC, with regard to the induction of GBP-1 by IFNs in FS2 fibroblasts protein synthesis may not be required to achieve the observed induction of GBP-1 mRNA. Therefore, cells were treated with the protein synthesis inhibitor cycloheximide (CHX) 15 minutes prior and during 5 hours incubation with IL-1 μ. Subsequently, the mRNA level of GBP-1 was measured by Northern blot hybridization. Therefore, aliquots of 30 μg of total cellular RNA were fractionated on a vertical 1% agarose/6% formaldehyde gel, transferred to a nylon membrane (Hybond N+ Amersham) and cross-linked by UV irradiation (264 nm, 2 min). The $^{32}$P-labelled DNA hybridization probes were prepared using a random prime labeling kit (Boehringer Mannheim, Germany). Hybridization was performed at 42° C. for 16 h in 50% formamide, 5×standard saline citrate (SSC), 10% dextran sulfate, 1% N-Lauroylsarcosine, 100 μg/ml sonicated salmon sperm DNA, and 250 μg/ml tRNA. Radioactively labeled probes ($2\times10^6$ cpm/ml with a specific activity>$6\times10$ cpm/μg DNA) were used for hybridization. After hybridization, the filters were washed with a final stringency of 0.1×SSC, 0.1% N-Lauroylsarcosine at 50° C. Autoradiography was performed with an intensifying screen at −70° C.

Under these conditions, CHX had no inhibitory effect on IL-1β-induced GBP-1 mRNA expression level. This suggests that all proteins necessary for the transcriptional response of GBP-1 to IL-1β in HDMVEC were pre-existent by the time IL-1β was added. Thus IL-1β, like IFN-γ in fibroblasts or HeLa, produced a rapid and durable induction of GBP-1 mRNA in HDMVEC in the absence of protein synthesis.

4. GBP-1 mRNA Expression is Induced by ICs but not by Angiogenic Growth Factors.

As GBP-1 was first described as an interferon-inducible protein, we investigated whether or not, in HDMVEC, IFN-γ, other ICs or growth factors known to activate endothelial cells could also regulate GBP-1 expression. HDMVEC were treated for 5 hours with or without IFN-γ (100 U/ml), TNF-α (300 U/ml), VEGF (10 ng/ml), or bFGF (10 ng/ml), and the GBP-1 expression was analyzed by Northern blot hybridization, as described above. It was shown that IL-1 β, IFN-γ and TNF-α dramatically upregulated the GBP-1 mRNA level in HDMVEC, whereas VEGF or bFGF did not. GBP-1 expression, which was specifically upregulated by ICs but not by angiogenic growth factors, thus represents a potential early marker for IC activation.

5. VEGF and bFGF Inhibit the IL-1β Induction of GBP-1 mRNA in HDMVEC.

It was further tested whether VEGF and/or bFGF could modulate the IL-1β-induced expression of GBP-1 mRNA. Therefore, HDMVEC were stimulated for 5 hours with IL-1β (20 U/ml) in the presence and absence of VEGF (10 ng/ml) and/or bFGF (10 ng/ml), and analyzed the GBP-1 mRNA level was analysed by Northern blot, as described above. It was shown that the presence of either VEGF or bFGF down-regulates the GBP-1 mRNA expression to 60% and 40% of the IL-1β induction (100%) respectively. When both angiogenic growth factors were added to the incubation medium simultaneously to IL-1β, the GBP-1 mRNA expression dropped dramatically to 17%. Thus, both angiogenic growth factors efficiently down-regulate the IL-1β-induced GBP-1 mRNA expression in HDMVEC. Furthermore, the GBP-1 mRNA expression appears not only to reflect IC activation but also the mutually exclusive molecular changes in the gene expression of endothelial cells promoted by ICs or growth factors.

6. VEGF and bFGF Inhibit the Binding of U937 Monocytes to IL-1β- or IFN-γ-Activated HDMVEC.

It was examined whether the VEGF- and bFGF-associated down-regulation of IL-1β-induced GBP-1 mRNA expression could correlate to any modulation in the biological activities of ICs. ICs are known to upregulate the expression of adhesion molecules on the surface of HDMVEC and to trigger the adhesion of the U937 moncytic cells to the activated endothelium. Therefore, we tested the influence of VEGF and bFGF on the IL-1β-induced adhesion competence of HDMVEC. HDMVEC were seeded at $10^4$ cells/$cm^2$ into 8-wells microchamber slides (Lab-Tek, Nunc Inc., Naperville, Ill.) and grown to 90% confluency in complete EBM/5%FBS (Clonetics). These subconfluent endothelial cells were treated for 6 hours with IL-1β at 20 U/ml with or without the addition of angiogenic growth factors. Then U937 moncytes were challenged for their ability to bind the cytokine-activated HDMVEC. For this, U937 moncytes were pre-incubated 30 min at 37° C. at $7\times10^5$ cells/ml in RPMI/1640 1% FBS, and then HDMVEC monolayers were incubated for 15 min with 500 μl of this U937 cell suspension. Non-adherent monocytes were gently washed out by floating the slides into RPMI/1640/1% FBS, and adherent cells were fixed 30 min by immersion in RPMI 1640/1% FBS (Gibco) containing 5% glutaraldehyde (Serva, Heidelberg, Germany). Adherent cells were then counted per arbitrary surface units using a computer program (Optimas, Unterhaching, Germany).

It was shown that simultaneous addition of IL-1β and either VEGF (10 ng/ml) or bFGF (10 ng/ml) reduced the number of adherent monocytes by more than 40% in comparison to experiments where only IL-1β was added. Reduction of the number of adhesive monocytes was even more pronounced (up to 60%) when both factors were combined. No significant activation of adhesion was seen when HDMVEC were treated with VEGF and/or bFGF alone. These data indicate that the ability of the HDMVEC to bind U937 monocytes correlates with the GBP-1 mRNA expression pattern. Interestingly, VEGF and/or bFGF also strongly inhibit (more than 50%) the adhesion of monocytes to IC-activated HDMVEC as they inhibit the GBP-1 expression. Taken together, these data suggested that in HDMVEC, the GTPase GBP-1 is involved in the signal pathways activated by ICs, leading to the adhesion competence of endothelial cells.

7. VEGF and bFGF Neutralize Growth Inhibition Induced by IL-1β and IFN-γ.

Another property of the inflammatory cytokines is their ability to inhibit cell proliferation (IL-1β and IFN-γ) or even induce the apoptosis (IFN-γ and TNF-α, of endothelial cells. Thus, it was examined whether VEGF and/or bFGF affect the growth inhibition induced by IL-1β or IFN-γ. For this purpose, HDMVEC were seeded into 12-multiwell plates (Costar) at $10^4$ cells/cm$^2$, maintained in low-serum medium for 24 h. The respective combination of factors was then added at adjusted concentrations in fresh low serum containing medium every second day. After 5 days of culture cells were washed in PBS, harvested by trypsination, and cell numbers were determined with a hemacytometer. Cells treated with VEGF (10 ng/ml) or bFGF (10 ng/ml) showed a 2- to 2.7-fold higher proliferation rate respectively to untreated control cells. By contrast, IL-1β (20 U/ml) or IFN-γ (100 U/ml) inhibited the proliferation of HDMVEC. However, the ability of HDMVEC to proliferate was restored when VEGF or BFGF were added to IL-1β, resulting in a 1.7- and 2-fold increase of proliferation rate in comparison to untreated control cells. The effect was even more pronounced when both, VEGF and bFGF, were simultaneously added to IL-1β treated cells. Also IFN-γ induced growth inhibition was counteracted by the addition of VEGF and/or bFGF. These results demonstrate that the GBP-1 expression inversely correlates with cell proliferation capacity of HDMVEC. In conclusion, GBP-1 plays an important role in the growth inhibition or apoptosis generated by ICs and counteracted by the growth factors.

Taken together the GBP-1 mRNA expression pattern correlated directly with the adhesion competence and inversely with the proliferation rate of the HDMVEC, suggesting that GTP-1 may regulate these two processes.

EXAMPLE 2

Overexpression of GBP-1 Gene in Sense or Antisense Orientation

1. Construction of GBP-1 Vectors

In order to obtain direct evidence of the role played by GBP-1 in IC-activated endothelial cells, as a functional test we investigated whether constitutive recombinant expression of GBP-1 may affect the biological properties of endothelial cells. Therefore, a GBP-1 expressing vector was constructed. For this, the full-length cDNA encoding GBP-1 was isolated using RT-PCR on total cellular RNA extracted from IFN-γ-treated HDMVEC and cloned into different vectors, as described in the following. Reverse transcription was performed on 5 μg of total cellular RNA pre-treated with DNase-I, using 2 pmol of the antisense oligonucleotide 5'-GCT CTA GAT TAG CTT ATG GTA CAT GCC TTT CG-3' (SEQ ID NO.: 4) binding as primer 1 to positions 1824 to 1847 of the published human GBP-1 cDNA (Cheng, Y. E., et al., 1988, *J. Interferon Res.*, 8:385–391), 0.5 μM of dNTPs and 200 units of the Superscript reverse transcriptase (Gibco BRL). PCR was performed on a tenth of the reverse transcription reaction with 10 pmol of the sense primer 2 (5'-CGG AAT TCG CCG CCA TGG CAT CAG AGA TCC ACA TG-3'; SEQ ID NO.: 5) and antisense primer 1 in a 100 μl final PCR reaction volume. The 30 cycles of amplification were as follow: denaturation 60 seconds at 94° C., primer annealing 60 seconds at 55° C., and extension 120 seconds at 72° C. This RT-PCR reaction gave rise to an 1801 bp product corresponding to the full-length coding sequence of GBP-1 flanked by the EcoRI and XbaI restriction sites. The PCR products were first inserted into the PCRScript vector (Stratagen) and fully sequenced. A cDNA encoding GBP-1 coding sequence, which was exactly the published sequence, was then cloned in the sense and antisense orientation into the EcoRI multiple cloning site of pCDNA3 (Invitrogen), pCDNA3-GFP (a gift from Dr. J. F. Giot) and the MoMuLV derived pBabePure vectors (Morgenstein, 1990).

2. Retroviral Particle Production and Infection

The packaging cell line PG13/J7 (Miller, 1991) was cultured in Dulbecco's modified medium supplemented with 10% heat inactivated foetal bovine serum (Gibco), 1× HAT (Gibco) and transfected overnight in 100 mm dishes (Falcon) by the calcium phosphate coprecipitation technique with 10 μg of the retroviral DNA constructs and 25 μg of carrier DNA. Two days post transfection 3 μg/ml puromycin (Sigma) was added to each culture. Viruses were obtained from isolated stable clones of the transfected cell lines. At 80% confluency medium was replaced by DMEM 10% FCS without puromycin. 12 hours later, the cell culture supernatants were harvested, and sterile filtered through a 0.45 μm filter.

Retroviral infection was performed by adding polybren to a final concentration of 8 μg/ml, and incubating the HDMVEC or HUVEC twice for 4 hours with neat or diluted supernatants, separated by an incubation with fresh normal endothelium medium (EBM 5% FBS) also for 4 hours. 48 hours after the infection, the cells were set under selection using 0.5 μg/ml of puromycin. The medium was replaced every third day until resistant colonies were visible.

The titers of the retroviral particles containing GBP-1 in sense or antisense orientation were compared by semi-quantitative RT-PCR. RNA from viruses were extracted from the supernatant using the High Pure viral RNA-kit (Boeringer Mannheim) as described by the manufacturer. RT-PCR was performed following the Titan one step reaction procedure (Boeringer Mannheim) with a set of primers specific for the GBP-1 coding sequence. RNA extracted from viral particles carrying GBP-1 sequences—in sense or antisense orientation—was either serially diluted and the different dilutions submitted to the same number of amplification cycles or a constant dilution was distributed to different experiments with the same number of PCR cycles. For each reaction, irrespectively of the experimental approach, identical results were obtained: in both cases (GBP-1 sense or antisense) the 950 bp amplification product was detectable at the same template dilution or number of cycles. This demonstrated that both viral stocks (sense, antisense construct) had the same titres.

3. Overexpression of GBP-1 Inhibits Endothelial Cell Proliferation

Primary human umbilical vein endothelial cells (HUVEC) were infected with retroviral vectors (pBabePuro) expressing GBP-1 mRNA in either sense (pBabePuroD16=D16) or antisense (pBabePuroD3=D3) orientation. The titers of pBabePuroD3 and pBabePuroD16 used for the infection were equivalent as evaluated with semi-quantitative RT-PCR. After 10 days of selection, numerous fast-growing puromycin resistant clones were obtained in experiments where an infection with the retroviral vector alone (pBabePuro) or pBabePuroD3 (antisense GBP-1) was performed. By contrast, only slowly growing clones were obtained from cells infected with pBabePuroD16 containing the sense GBP-1. These results already suggested that GBP-1 may function as a growth inhibitor in HUVEC. The characterization of the transgene expressions was confirmed by Northern blot analysis using the 300 bp internal fragment of GBP-1 and a gag-pol fragment of MMLV as probes. As expected, the expression of the retroviral gag-encoding mRNA (2.5 kb) was detected in pBabePuro transduced control cells. In cells transduced with pBabePuroD3 or pBabePuroD16, respectively, a 4.4 kb mRNA encoding part of the retroviral gag sequences (2.5 kb) and GBP-1 mRNA sequences (1.8 kb) were detected. When assayed for their proliferation capacity over a period of 6 days, endothelial cells constitutively expressing recombinant GBP-1 (D16) clearly grew slower than control cells or cells expressing GBP-1 mRNA in antisense orientation (D3). Furthermore, in the presence of increasing concentrations of VEGF and bFGF (1, 10, 100 ng/ml) cells transduced with pBabePuroD16 reached only 58% of the proliferation rates obtained with pBabePuro transduced control cells under these conditions. These data demonstrate that the expression of GBP-1 in endothelial cells inhibits cell proliferation.

4. Overexpression of Antisense GBP-1 mRNA in Endothelial Cells Counteracted the Growth Inhibition Induced by IL-1β or IFN-γ.

Finally, it was investigated whether inhibition of cellular GBP-1 expression by recombinant expression of GBP-1 antisense mRNA in endothelial cells may affect the antiproliferative effect of the inflammatory cytokines.

HUVECs transduced with pBabePuroD3 and thus, constitutively expressing high levels of antisense GBP-1 mRNA, and control cells transduced with pBabePuro were cultivated with VEGF and bFGF (10 ng/ml each) in a low-serum medium, and were simultaneously exposed to increasing concentrations of IL-1β (2–200 U/ml) or IFN-γ (10–1000 U/ml). After 6 days of culture cell numbers were determined. In both cases IL-1β or IFN-γ decreased in a dose-dependant manner the proliferation induced by the growth factors. However, pBabePuroD3 transduced cells were clearly less sensitive than the control cells, showing only 62% and 27% growth inhibition compared to 17% and 15% in the presence of highest concentrations of IL-1β and IFN-γ, respectively. The expression of antisense GBP-1 mRNA in pBabePuroD3 transduced cells potently protected the endothelial cells from the IC-induced inhibition of cell proliferation. These data fully confirmed the role played by GBP-1 in the inhibition of endothelial cell proliferation.

EXAMPLE 3

Visualization of GFP-GBP-1 in Transfected Cells

In order to investigate whether the cloned cDNA may encode a full length functional GBP-1 protein the molecular weight of the encoded protein was determined by Western blotting and localization studies of GBP-1 in the cell were carried out.

GBP-1 protein carries a CAAX isoprenylation signal motif at the C-terminus that was shown to be functional in vitro and in vivo, suggesting that GBP-1 may be a membrane-associated protein. To investigate localization of the GBP-1 protein in eukaryotic cells cDNA encoding a chimeric protein of the green fluorescent protein (GFP) from the jellyfish *Aequorea victoria* and GBP-1 was constructed. Thus, the GFP was fused to the N-terminus of the GBP-1 protein to prevent any interference with the isoprenylation motif CAAX located at the C-terminus. Therefore, the full-length GBP-1 cDNA was inserted in frame with a GFP CDNA (GFP-GBP-1) in the mammalian expression vector pCDNA3. With this plasmid the inserted cDNA can be highly expressed under control of T7-RNA polymerase in eukaryotic cells. T7-RNA polymerase expression is triggered in respective cells by superinfection with a vaccinia virus encoding T7-RNA polymerase. CV1 were seeded in 6-well plates until they reached 80% confluency washed with Optimem (Gibco) and infected for one hour at 37° C. with $10^6$PfU per well of T7-RNA polymerase encoding Vaccinia virus, in DMEM/0%FBS. After one wash with Optimem, transfection was performed by incubating the cells overnight in a solution of Optimem containing 7 μl lipofectamine and 2 μg plasmid per well. CV1 cells were then washed in PBS and fixed 15 min at room temperature in 2% formaldehyde, 2% glutaraldehyde, 1×PBS solution. Visualization of the GFP or GFP-GBP-fusion proteins was achieved by fluorescence microscopy. Cells transfected with the constructs encoding GFP alone or fused to GBP-1 antisense displayed a diffuse fluorescence evenly distributed throughout the cytoplasm and slightly concentrated in the nucleus. This distribution was consistent with previous reports on the diffuse cellular localization of GFP. By contrast, the expression of GFP-GBP-1 protein resulted in an intense and punctuated perinuclear fluorescence pattern. This suggested an association with inner cell membranes and was reminiscent of the characteristic pattern displayed by proteins when localized at the intracellular membranes of the Golgi apparatus. This distinct localization was consistently and reproducibly obtained in CV1, but also in other cell types investigated such as CHO, NIH-3T3, and HeLa cells.

Western blot analysis of the transfected cells with an anti-GFP antibody confirmed the expression in CV1 of the GFP (27 kDa) or GFP-GBP-1 fusion proteins (97 kDa). For the Western blot analysis CV1 cells were grown in T75 $cm^2$ flasks until they reached 80% confluency and transfected using Lipofectamine (Gibco). After 12 h cells were harvested and protein extracts were prepared using the RIPA buffer (150 mM NaCl, 1% Na-Deoxycholate, 1% triton X-100, 0.1% dodecyl sulfate (SDS) and 10 mM Tris-Cl pH 8.5) (Roux 1982) and sonification. Protein extracts were boiled in 1× Laemmli buffer (50 mM Tris/HCl pH6.8, 100 mM dithiothreitol (DTT), 2% SDS, 0.1% bromophenol blue, and 10% glycerol) and subjected to SDS (12%) polyacrylamide gel electrophoresis (PAGE) in the presence of 10% β-mercaptoethanol (reducing conditions). Proteins were then electrophoretically transferred to a 0.2-μm PVDF membrane (Pall Filtron) using a semi-dry blotting apparatus. Immunostaining was performed using a mouse monoclonal anti-GFP antibody (Boehringer Mannheim) and a horseradish-peroxidase-conjugated anti-mouse IgG antibody (Dako Diagnostika, Hamburg, Germany). Immunocomplexes were visualized using the chemoluminescence detection system (ECL) (Amersham Buchler, Braunschweig, Germany). Detection of a 97 kDa protein (27 kDa from the GFP part and 70 kDa from the GBP-1 part) in the extracts of cells transfected with the cDNA encoding the GFP-GBP-1 fusion protein clearly proofs that the isolated cDNA encodes a full-length GBP-1 protein.

EXAMPLE 4

In Situ Hybridization and Immunohistochemistry

To verify the in vivo biological relevance of GBP-1 expression, Kaposi's sarcoma (KS) lesions were studied, since KS is an endothelial cell-derived angioproliferative tumor characterized by lymphocyte and monocyte infiltration and production of IFN-γ, TNF-α and IL-1β in early-stage lesion areas and by angiogenic growth factor (AGF) production in late-stage areas. In fact, early-stage areas are characterized by incompletely formed dilated or slit-like vascular structures and prominent extravasation of lymphocytes and monocytes that express high amounts of inflammatory cytokines (IC), whereas later stages are characterized by proliferating endothelial cell-derived tumor cells, the so-called KS spindle cells, and by high expression of VEGF and bFGF. Early- and late-stage areas often co-exist in one lesion.

The method of in situ hybridization and immunohistochemistry was performed in the following manner. KS specimens were derived from human immunodeficiency virus (HIV)-1-infected homosexual male patients classified as Center for Disease Control group C. None of the patients received anti-KS therapy prior to the biopsy. Control skin biopsies were obtained from an uninvolved area. All biopsies were taken for diagnostic purposes after the informed consent of the patients. The plasmid pCR-ScriptTM SK(+) (Stratagene) containing the full length GBP-1 cDNA was used for the synthesis of 35S-radiolabeled sense and antisense RNA hybridization probes.

The proliferation-associated antigen Ki67 was detected by immunohistochemistry using a monoclonal mouse anti-Ki67 antibody (MIB-1) (Dianova, Hamburg, Germany) at 1:10 dilution (overnight at 4° C.). The bound primary antibody was then detected with a commercially available Super Sensitive detection kit (BioGenex) with an alkaline phosphatase reaction using the fast red chromogen (Sigma, Deisenhofen, Germany) as a substrate.

In these studies, it was shown that the GBP-1 expression correlates inversely with endothelial spindle cell proliferation in Kaposi's sarcoma. In all of 5 KS lesions examined prominent signals were obtained by in situ-hybridization with the GBP-1 antisense probe in several distinct patches of early-stage areas that were located at the boundaries of the KS tissue and around dilated vessels and are characterized by numerous incomplete slit-like vascular spaces filled with erythrocytes. By contrast, signal intensity was significantly reduced or absent in late-stage areas with bundles of proliferating KS spindle cells. Peritumoral tissues were mostly negative with the exception of a few well-differentiated vessels. A higher magnification of two positive vessels in the peritumoral area demonstrated that GBP-1, in fact, is expressed also in normal endothelial cells in vivo. By combining GBP-1 in situ-hybridization and immunohistochemical detection of the proliferation-associated antigen Ki67 on consecutive KS tissue sections, Ki67 expression was found to be low in areas with high GBP-1 expression, whereas GBP-1 expression was low in areas with numerous proliferating spindle cells. Tissue sections of healthy skin of a KS patient did not show signals with the GBP-1 antisense probe. In addition, no signals were observed by hybridization with the GBP-1 sense control probe. These data demonstrated that also in endothelial cells in vivo GBP-1 expression is associated with the IC-activated non-proliferative phenotype.

While this invention has been particularly shown and described with references to preferred embodiments thereof, it will be understood by those skilled in the art that various changes in form and details may be made therein without departing from the scope of the invention encompassed by the appended claims.

What is claimed is:

1. An oligonucleotide hybridizing under stringent conditions to a nucleic acid sequence encoding the GBP-1 gene, a part thereof or a regulatory element thereof, wherein said oligonucleotide consists of a nucleic acid sequence selected from the group consisting of: SEQ ID NO: 1, SEQ ID NO: 2, SEQ ID NO: 3, SEQ ID NO: 4, and SEQ ID NO: 5.

2. A method for detecting GBP-l gene expression in a sample comprising:
   a) contacting the sample with at least one oligonucleotide consisting of a nucleic acid sequence selected from the group consisting of SEQ ID NO: 1, SEQ ID NO: 2, SEQ ID NO: 3, SEQ ID NO: 4 and SEQ ID NO: 5, under conditions in which a hybridization complex forms between GBP-1 and said oligonucleotide;
   b) determining whether the hybridization complex is present,
wherein if the hybridization complex is present then GBP-1 gene expression is detected.

3. A diagnostic component comprising at least one oligonucleotide, wherein said oligonucleotide hybridizes under stringent conditions to GBP-1, a part thereof, or a regulatory element thereof, and wherein said oligonucleotide consists of a nucleic acid sequence selected from the group consisting of SEQ ID NO: 1, SEQ ID NO: 2, SEQ ID NO: 3, SEQ ID NO: 4 and SEQ ID NO: 5.

4. A diagnostic kit comprising at least one oligonucleotide, wherein said oligonucleotide hybridizes under stringent conditions to GBP-1, a part thereof, or a regulatory element thereof, and wherein said oligonucleotide consists of a nucleic acid sequence selected from the group consisting of SEQ ID NO: 1, SEQ ID NO: 2, SEQ ID NO: 3, SEQ ID NO: 4 and SEQ ID NO: 5.

5. A method for quantifying GBP-1 gene expression in a sample comprising
   a) contacting the sample with at least one oligonucleotide consisting of a nucleic acid sequence selected from the group consisting of SEQ ID NO: 1, SEQ ID NO: 2, SEQ ID NO: 3, SEQ ID NO: 4 and SEQ ID NO: 5, under conditions in which a hybridization complex forms between GBP-1 and said oligonucleotide;
   b) detecting the presence of the hybridization complex;
   c) quantifying GBP-1 in said hybridization complex,
thereby quantifying GBP-1 expression in said sample.

6. The method of claim 5, wherein said method further comprises amplifying a nucleic acid sequence encoding GBP-1, a part thereof, or a regulatory element thereof.

7. The method of claim 2, wherein said method further comprises amplifying a nucleic acid sequence encoding GBP-1, a part thereof, or a regulatory element thereof.

8. The diagnostic kit of claim 4, wherein said oligonucleotide is attached to a solid support.

9. An oligonucleotide consisting of SEQ ID NO: 1.

10. An oligonucleotide consisting of SEQ ID NO: 2.

11. An oligonucleotide consisting of SEQ ID NO: 3.

12. An oligonucleotide consisting of SEQ ID NO: 4.

13. An oligonucleotide consisting of SEQ ID NO: 5.

* * * * *